United States Patent
Saito et al.

(10) Patent No.: US 6,495,365 B1
(45) Date of Patent: Dec. 17, 2002

(54) HEMATOPOIETIC STEM CELL PROLIFERATING AGENTS

(75) Inventors: Yoshimasa Saito, Kawanishi (JP); Yoshiko Ueda, Osaka (JP); Kouichi Tamura, Kobe (JP); Yoko Takata, Osaka (JP); Hisashi Yamada, Sanda (JP); Tatsuo Yamashita, Kobe (JP); Masakazu Kobayashi, Takarazuka (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/147,689

(22) PCT Filed: Aug. 12, 1997

(86) PCT No.: PCT/JP97/02818

§ 371 (c)(1),
(2), (4) Date: May 13, 1999

(87) PCT Pub. No.: WO98/06422

PCT Pub. Date: Feb. 19, 1998

(30) Foreign Application Priority Data

Aug. 13, 1996 (JP) ............................................. 8/213641
Jan. 24, 1997 (JP) ............................................... 9/11054

(51) Int. Cl.$^7$ ................................................. C12N 5/00
(52) U.S. Cl. ........................... 435/387; 435/372; 514/2; 514/21; 530/351
(58) Field of Search ....................... 514/2, 21; 530/351; 435/372, 387

(56) References Cited

U.S. PATENT DOCUMENTS 5,397,706 A * 3/1995 Correa et al. .......... 435/240.31
5,733,541 A * 3/1998 Taichamn et al. .......... 424/93.1
6,011,000 A * 1/2000 Perrine et al. ................. 514/2

FOREIGN PATENT DOCUMENTS

| EP | 230980 | * | 8/1987 |
| WO | 93/09220 | | 5/1993 |

OTHER PUBLICATIONS

Journal of Cellular Physiology, vol. 157, No. 1, p. 178–183.
Blood, vol. 86, No. 2 (1995) p. 572–580.
The Journal of Clinical Investigation, vol. 94, No. 1 (1994), p. 34–43.
Oncogene, vol. 7, No. 11 (1992) p. 2243–2248.
Stem Cells, vol. 15, No. 3 (1997) p. 214–222.

* cited by examiner

*Primary Examiner*—Jean C. Witz
(74) *Attorney, Agent, or Firm*—Oblon, Spivak, McClelland, Maier & Neustadt, P.C.

(57) ABSTRACT

This invention relates to a hematopoietic stem cell proliferating agent comprising IGF-I, a hematopoietic stem cell proliferating agent comprising IGF-I and at least one protein selected from among SCF, M-CSF, and G-CSF, and a method of growing hematopoietic stem cells which comprises culturing hematopoietic stem cells in a medium containing IGF-I and at least one protein selected from the group consisting of SCF and M-CSF.

The hematopoietic stem cell proliferating agent of the invention causes hematopoietic stem cells to proliferate in the undifferentiated state whether in vivo or in vitro and can, therefore, be used for amelioration of the cytopenia induced by radiotherapy or chemotherapy using anticancer drugs, prevention of infectious diseases associated with lymphopenia, or in vitro culture for multiplication of hematopoietic stem cells and extrasomatic culture of recombinant stem cells in gene therapy.

16 Claims, No Drawings

HEMATOPOIETIC STEM CELL PROLIFERATING AGENTS

TECHNICAL FIELD

This invention relates to a hematopoietic stem cell proliferating agent and a method for stimulating the proliferation. More particularly, the invention relates to a hematopoietic stem cell proliferating agent comprising insulin-like growth factor I either alone or in combination with some or other colony-stimulating factors and/or growth factors and to a method for proliferating.

BACKGROUND ART

A variety of growth factors relating to the blood system are under investigation, and erythropoietin (EPO) as an erythropoiesis stimulating agent and granulocyte colony-stimulating factor (G-CSF) as a leukopoiesis stimulating agent, among others, have been clinically put to use to this day. Regarding the technology for proliferating of hematopoietic stem cells, various cytokines such as stem cell factor (SCF), macrophage colony-stimulating factor (M-CSF), etc. were explored but none has been found to be effective enough in causing hematopoietic stem cells to multiply sufficiently in the undifferentiated form.

As the result of an intensive investigation, the inventors of this invention found that hematopoietic stem cells can be successfully caused to multiply in the undifferentiated state well by using insulin-like growth factor I (IGF-I) in combination with at least one protein selected from among SCF, M-CSF, and G-CSF. This invention has been developed on the basis of the above finding.

DISCLOSURE OF THE INVENTION

This invention relates to a hematopoietic stem cell proliferating agent comprising IGF-I, a hematopoietic stem cell proliferating agent comprising IGF-I and at least one protein selected from among SCF, M-CSF, and G-CSF, and a method of stimulating proliferation of hematopoietic stem cells which comprises culturing hematopoietic stem cells in a culture medium containing IGF-I and at least one protein selected from among SCF, M-CSF, and G-CSF. Furthermore, this invention relates to a method of proliferating of hematopoietic stem cells in a mammal which comprises using IGF-I alone or in combination with at least one protein selected from among SCF, M-CSF, and G-CSF.

Since the hematopoietic stem cell proliferating agent and method of the invention are effective in causing hematopoietic stem cells to multiply in the undifferentiated state whether in vivo or in vitro, the invention finds application in the management of the cytopenia induced by radiotherapy or chemotherapy using anticancer drugs, prevention of infectious diseases with which lymphopenia is associated, treatment of myelopathy inclusive of osteomyelodysplasia and bone marrow suppression, therapy of marrow diseases such as leukemia-advanced renal impairment-bone marrow suppression, improvement in engraftment survival in bone marrow transplantation, therapy of hypocytosis associated with inherited diseases, in vitro culture for multiplication of hematopoietic stem cells, and extrasomatic culture of recombinant stem cells in gene therapy, among other uses.

The IGF-I which can be used in this invention includes the corresponding proteins derived from human, bovine, and other mammals by recombinant DNA technology (e.g. Kokai Tokkyo Koho S61-1396 for IGF-I), peptide synthesis, cell culture, or other technology and even the muteins having IGF-I activity which can be derived from the recombinant or other IGF-I by partial modification of its amino acid sequence by substitution, insertion, addition, or deletion of one or more amino acid residues (e.g. WO89/05822).

The SCF, M-CSF, or G-CSF which can be used in this invention includes the corresponding proteins derived from human, bovine, or other mammals by recombinant DNA technology, peptide synthesis, cell culture, or other technology and even those muteins having SCF, M-CSF, or G-CSF activity which can be derived from the recombinant or other SCF, M-CSF or G-CSF by partial modification of its amino acid sequence by substitution, insertion, addition, or deletion of one or more amino acid residues. Here, the sugar chain may be present or absent.

The hematopoietic stem cell proliferating agent of this invention which comprises IGF-I and either SCF, M-CSF, or G-CSF can be administered virtually without limitations on the dosage form or forms, sequence of administration, or route of administration, all that is necessary being to insure that those factors will be concurrently available in the recipient's body. For example, they can be administered as a mixture in a single dosage form or in independent dosage forms, whether concurrently or one after another, and whether by the same route or by different routes.

The hematopoietic stem cell proliferating agent of the invention is generally provided in an oral dosage form or in a nonoral dosage form, e.g. an injection, drip infusion, transdermal therapeutic system, transnasal therapeutic system, external preparation, suppository, etc., each containing IGF-I alone or IGF-I plus at least one protein selected from among SCF, M-CSF and G-CSF together with a carrier (e.g. distilled water for injection, physiological saline, glucose injection, etc.), a stabilizer (e.g. albumin, sodium citrate, arginine, dextran, etc.), a pH control agent (e.g. sodium monohydrogen phosphate, sodium dihydrogen phosphate, etc.) and other additives. Such dosage forms or systems may further contain one or more growth factors such as SCF, M-CSF, G-CSF, EPO, and IL-3.

The dosage of this hematopoietic stem cell proliferating agent depends on the patient's body weight, sex, and clinical condition but the dose level for an adult human is generally about 1~1000 µg/kg in terms of IGF-I and preferably about 5~500 µg/kg on the same basis. When SCF, M-CSF, or G-CSF is used concomitantly, SCF, M-CSF or G-CSF can be formulated in the same amount as IGF-I or in an amount ranging from 0.01 to 100 times the amount of IGF-I.

This hematopoietic stem cell proliferating agent can be administered orally or otherwise, e.g. by intravenous injection, intravenous drip, subcutaneous injection, coronary intraarterial administration, transdermal administration, transnasal administration, or rectal administration.

IGF-I and any of SCF, M-CSF and G-CSF can be formulated in one and the same dosage form but may be administered independently one after the other or concurrently, either by the same route or different routes. When they are administered in sequence, it does not matter which is administered first.

When the hematopoietic stem cell proliferating agent of the invention is used for ameliorating the cytopenia induced by radiotherapy or chemotherapy using anticancer drugs, the hematopoietic stem cell proliferating agent of the invention can be used alone or concurrently with EPO, M-CSF, SCF, IL-3, G-CSF, and/or the like. When it is used for the prevention of infectious diseases associated with lymphopenia, GM-CSF or the like can be used concomitantly. Furthermore, in the treatment of myelopathies such as osteomyelodysplasia and bone marrow suppression or marrow diseases such as leukemia-advanced kidney impairment-bone marrow suppression, for improvement in engraftment survival in bone marrow transplantation, or in the treatment of hypocytosis associated with inherited diseases, suitable growth factors such as EPO, G-CSF, GM-CSF, etc. can be used as concomitant medications.

In the in vitro culture for multiplication of hematopoietic stem cells or extrasomatic culture of recombinant stem cells in gene therapy, among other applications, the hematopoietic stem cell proliferating agent of the invention can be used in combination with other suitable growth factors. In vitro culture of marrow cells can be essentially carried out in accordance with the method described in Shin Seikagaku Jikken Koza [New Biochemical Experiment Series] 18 Saibo Baiyo Gijutsu [Cell Culture Technology] (ed. by Japanese Biochemical Society, Tokyo Kagaku Dojin, 1989). For example, using a $CO_2$ incubator, marrow cells can be cultured in RD medium [RPMI1640:DMEM=1:1 (v/v)] supplemented with insulin, transferring, 2-mercaptoethanol, ethanolamine, selenious acid, HEPES, etc. in the presence of IGF-I (1~1000 g g/ml) and at least one protein selected from among SCF (1~1000 μg/ml), M-CSF (1~1000 μg/ml), and G-CSF (1~1000 μg/ml).

BEST MODE FOR CARRYING OUT THE INVENTION

This invention is now described in further detail by way of the following examples.

EXAMPLE 1
Procurement of Hematopoietic Stem Cells

Using the femora of male C57BL mice (10 individuals), marrow cells were recovered in α-MEM (5 ml, Nikken Biomedical Research Institute). This cell suspension was centrifuged (1,200 rpm, 10 min.), the supernatant was aspirated off, and the cells were resuspended in 10% FCS-α-MEM (5 ml) By this procedure, approximately $3 \times 10^7$ marrow cells per mouse were harvested.

EXAMPLE 2
FACS

From the marrow cells thus procured, Sca-1+, Lin−, and c-kit+ cells were collected using Fac-Scan flow cytometer (Becton-Dickinson). The labeled antibodies used are shown in Table 1. It is known from the literature that the cell fraction thus obtained contains murine hematopoietic stem cells [Okada, S. et al. (1992), Blood 80, 3044–3050].

TABLE 1

Labeled antibodies used in FACS

| Marker | Labeled antibody | Specificity |
|---|---|---|
| Lin | Biotinylated anti-CD3 ε (Clone 500A2) | T cell |
| | Biotinylated anti-CD45R (B220) | B cell |
| | Biotinylated anti-mouse erythrocytes (TER119) | Erythrocyte |
| | Biotinylated anti-CD11b (Mac-1) | Monocyte/macrophage |
| | Biotinylated anti-myelocyte differentiation antigen (Gr1) | Granulocyte |
| Sca-1 | PE-labeled anti-mouse SCA-1 (E13-161.7) | Stem cell |

TABLE 1-continued

Labeled antibodies used in FACS

| Marker | Labeled antibody | Specificity |
|---|---|---|
| c-kit | PITC-labeled anti-mouse CD117 (3CI) | SCF receptor |

EXAMPLE 3
Action of IGF-I

A U-bottomed 96-well microtiter plate (Nunc, Denmark) was seeded with hematopoietic stem cells at a density of 50 cells/10% FCS-a -MEM (100 μl)/well.

To each well was added IGF-I (Mecasermin, recombinant, Fujisawa Pharmaceutical) (100 ng/ml) SCF (recombinant, Genzyme) (1.5, 3.0, 6.0, 12.5, 25 ng/ml) +IGF-I (100 ng/ml), or M-CSF (recombinant, R&D System)- (0.1, 0.3, 1.0, 3.0, 10, 30, 100 ng/ml)+IGF-I (100 ng/ml) and the plate was incubated in a $CO_2$ incubator at 37° C. for 10 days.

After 6 days of culture, the cells in each well were counted.

After 10 days of culture, the medium was aspirated off and the cytoplasmic acid phosphatase activity was assayed by the method described in the literature [Uedaetal. (1994), Neurosci. Lett., 165, 203–207].

EXAMPLE 4
Results

The results are summarized in Table 2.

TABLE 2

Effect of the combination of IGF-I with either SCF or M-CSF

| IGF-I (ng/ml) | Factor added (ng/ml) | Δ 450 means ± SD |
|---|---|---|
| 100 | SCF 25.0 | 1.387 ± 0.207 |
| 100 | SCF 12.5 | 0.654 ± 0.273 |
| 100 | SCF 6.0 | 0.056 ± 0.015 |
| 100 | SCF 3.0 | 0.035 ± 0.010 |
| 0 | SCF 25.0 | 0.176 ± 0.074 |
| 100 | M-CSF 100.0 | 0.906 ± 0.645 |
| 100 | M-CSF 30.0 | 0.778 ± 0.649 |
| 100 | M-CSF 10.0 | 0.564 ± 0.402 |
| 100 | M-CSF 3.0 | 0.064 ± 0.050 |
| 0 | M-CSF 100.0 | 0.052 ± 0.045 |
| 100 | None | ND |

ND: below detection limit

It will be apparent from Table 2 that IGF-I as used in combination with SCF or M-CSF increased the cytoplasmic acid phosphatase activity of the marrow cell fraction obtained in Example 2. It is known that cytoplasmic acid phosphatase activity increases in proportion to an increase in the cell population. Therefore, it is clear that IGF-I as used in combination with SCF or M-CSF exerted a hematopoietic stem cell proliferation stimulating action. It is known from the literatrue that SCF and M-CSF each independently does not show hematopoietic stem cell proliferation stimulating activity [Okada, S. et al. (1992), Blood 80, 3044-3050] and the inventors verified the finding.

EXAMPLE 5
FACS

Using the same procedure as used in Example 2, Lin−, Sca-1+, c-kit+, and CD34− cells were harvested. For selection of CD34− cells, biotinylated anti-mouse CD34 (RAM34) (Fermigen, San Diego, Calif.) was newly used.

Those cells accounted for about 0.04% of the total marrow cell population. It is known from the literature that cells of this group are hematopoietic stem cells (Ohsawa & Nakauchi 1995, Japanese Molecular Biochemical Society S4B-3; Ohsawa et al. 1995, Synopsis of Blood Stem Cell Symposium).

EXAMPLE 6
Effect of IGF-I

Using ACDU, the cells obtained in Example 5 were transferred to 96-well plates, one cell per well, and about 50 wells were used as one group.

To each well was added SCF (25 ng/ml)+IGF-I (100 ng/ml), M-CSF (100 ng/ml)+IGF-I (100 ng/ml) or SCF (25 ng/ml)+IL-3 (10 ng/ml), and the plates were incubated in a $CO_2$ incubator at 37° C. for 10 days.

After 6 days of culture, the cells in each well were counted.

After 10 days of culture, the medium was aspirated off from each well and the cytoplasmic acid phosphatase activity was assayed.

EXAMPLE 7
Results

The results are summarized in Table 3.

TABLE 3

Effect of the combination of IGF-I with either SCF or M-CSF on the single cell

|  | Surviving wells/ all wells (survival rate) | Mean number of surviving cells/ well |
|---|---|---|
| IGF-I (100 ng) + SCF (25 ng/ml) | 25/47 (53%) | 10 |
| IGF-I (100 ng) + M-CSF (100 ng/ml) | 3/47 (6.0%) | 2 |
| Medium | 0/23 (0.0%) | 0 |
| IL-3 (10 mg) + SCF (25 ng/ml) | 33/48 (69%) | NT |

NT: not counted

It will be apparent from Table 3 that IGF-I as used in combination with SCF or M-CSF is capable of causing proliferation of singular hematopoietic stem cells.

EXAMPLE 8
Immunostaining

Sca-1$^+$, Lin$^-$, and c-kit$^+$ cells were collected by the same procedure as in Examples 1 and 2. The harvested cells were seeded on a 100-well chamber slide (Lab-Tek, Nunc). In a $CO_2$ incubator at 37° C., the cells were cultured in 10% FCS-a-MEM (100 µl) containing growth factors [IGF-I (100 ng/ml) and SCF (25 ng/ml)] for 8 days.

The cultured cells were fixed with acetone (−20° C.) on the slide. After addition of 1% BSA-phosphate buffer for inhibition of nonspecific binding, the cells were treated with the antibodies shown in Table 4.

The cells were not stained by any of the antibodies used, indicating that they had no tendency toward differentiation to any specific kinds of offspring cells. The augmentation of cell population by IGF-I plus SCF was not the proliferation due to differentiation of stem cells but the proliferation of undifferentiated stem cells.

TABLE 4

Labeled antibodies used in FACS

| Marker | Labeled antibody | Specificity |
|---|---|---|
| Lin | Biotinylated anti-CD3 Δ (Clone 500A2) | T cell |
|  | Biotinylated anti-CD45R (B220) | B cell |
|  | Biotinylated anti-mouse erythrocytes (TER119) | Erythrocyte |
|  | Biotinylated anti-CD11b (Mac-1) | Monocyte/ macrophage |
|  | Biotinylated anti-myelocyte differentiation antigen (Gr1) | Granulocyte |
| Sca-1 | PE-labeled anti-mouse SCA-1 (E13-161.7) | Stem cell |

EXAMPLE 9
The Action of Human G-CSF Plus Human IGF-I

Hematopoietic stem cells were transferred to a U-bottomed 96-well microtiter plate (Nunc, Denmark), 50 cells/10% FCS-α-MEM (100 µl)/well.

To each well was added human IGF-I (Mecasermin, recombinant, Fujisawa Pharmaceutical) (100 ng/ml) or human G-CSF (recombinant, R&D System) (5, 50, or 500 mg/ml)+IGF-I (100 ng/ml), and the plate was incubated in a $CO_2$ incubator at 37° C.

After 7 days of culture, the medium was aspirated off from each well and the cytoplasmic acid phophatase activity was assayed by the method described in the literature (Ueda et al. (1994), Neurosci. Lett., 165, 203–207).

EXAMPLE 10
Results

The results are summarized in Table 5.

TABLE 5

| G-CSF (ng/ml) | IGF-I (ng/ml) | Δ 450 mean ± SE |
|---|---|---|
| 500 | 100 | 0.164 ± 0.033 |
| 50 | 100 | 0.132 ± 0.086 |
| 5.0 | 100 | 0.126 ± 0.071 |
| 0.50 | 100 | 0.038 ± 0.020 |
| 0 | 100 | 0.001 ± 0.004 |
| 500 | 0 | 0.054 ± 0.007 |
| 50 | 0 | 0.015 ± 0.019 |
| 5.0 | 0 | 0.010 ± 0.014 |
| 0.50 | 0 | 0.008 ± 0.003 |
| 0 | 0 | 0.000 ± 0.002 |

It will be apparent from Table 5 that IGF-I as used in combination with G-CSF enhanced the cytoplasmic acid phosphatase activity of the marrow cell fraction obtained in Example 2. It is known that cytoplasmic acid phosphatase activity is positively correlated with the number of cells. Therefore, it is evident that IGF-I as used in combination with G-CSF exhibited a hematopoietic stem cell proliferation stimulating action. No effect was found with G-CSF alone.

EXAMPLE 11
The Action of Human SCF Plus Human IGF-I

Hematopietic stem cells were transferred to a U-bottomed 96-well microtiter plate (Nunc, Denmark), 50 cells/10% FCS-α-MEM (100 µl)/well.

To each well was added human SCF (recombinant, R&D System) (5,50, or 500 mg/ml)+IGF-I (100 ng/ml), and the plate was incubated in a $CO_2$ incubator at 37° C.

After 7 days of culture, the cells in each well were counted.

EXAMPLE 12

Results

The results are summarized in Table 6.

TABLE 6

| SCF (ng/ml) | Mean ± SE (IGF-I 100 ng/ml) | Mean ± SE (IGF-I 0 ng/ml) |
| --- | --- | --- |
| 800 | 200 ± 0.0 | 75.7 ± 26.4 |
| 400 | 175 ± 21.5 | 36.0 ± 14.3 |
| 200 | 58.0 ± 16.7 | 14.8 ± 8.2 |
| 100 | 31.5 ± 6.2 | 9.8 ± 1.6 |
| 50 | 16.0 ± 5.5 | 6.5 ± 5.0 |
| 25 | 6.3 ± 2.9 | 3.5 ± 0.5 |
| 12.5 | 3.8 ± 1.5 | 2.0 ± 0.7 |
| 6.25 | 3.3 ± 0.8 | 3.0 ± 3.7 |
| 3.0 | 3.5 ± 1.1 | 2.3 ± 1.1 |
| 0 | 2.8 ± 2.2 | 1.0 ± 1.0 |

It will be apparent from Table 6 that IGF-I as used in combination with SCF stimulated proliferation of hematopoietic stem cells to a remarkable extent. This combination is, therefore, useful for the maintenance and multiplication of hematopoietic stem cells.

EXAMPLE 13

Pharmaceutical Preparations

The components indicated in Table 7 were dissolved in water and vials filled with 5 ml portions of the respective solutions were lyophilized to provide hematopoietic stem cell proliferating agents.

TABLE 7

Examples of the hematopoietic stem cell proliferation stimulating composition

| | IGF-I (mg) | SCF (mg) | M-CSF (mg) | G-CSF (mg) | Human albumin (mg) |
| --- | --- | --- | --- | --- | --- |
| Composition 1 | 10 | 0 | 0 | 0 | 0 |
| Composition 2 | 10 | 0 | 0 | 0 | 50 |
| Composition 3 | 10 | 20 | 0 | 0 | 50 |
| Composition 4 | 10 | 0 | 10 | 0 | 50 |
| Composition 5 | 10 | 0 | 0 | 10 | 50 |
| Composition 6 | 5 | 10 | 10 | 0 | 0 |
| Composition 7 | 5 | 0 | 5 | 5 | 100 |
| Composition 8 | 5 | 10 | 0 | 5 | 100 |
| Composition 9 | 5 | 5 | 5 | 5 | 50 |

INDUSTRIAL APPLICABILITY

Thus, the hematopoietic stem cell proliferating agent and method of the invention are of great utility value, for hematopoietic stem cells can be caused to proliferate in the undifferentiated state whether in vivo or in vitro.

What is claimed is:

1. A method of proliferating hematopoietic stem cells consisting essentially of culturing hematopoietic stem cells in a medium consisting essentially of IGF-I and at least one protein selected from the group consisting of M-CSF and G-CSF.

2. The method of proliferating hematopoetic stem cells according to claim 1 wherein said medium consists essentially of IGF-I and M-CSF.

3. The method of proliferating hematopoetic stem cells according to claim 1 wherein said medium consists essentially of IGF-I and G-CSF.

4. The method of claim 1, wherein the IGF-I is in a concentration of from 1 to 1000 μg/ml of medium.

5. The method of claim 1, wherein the medium consists essentially of IGF-I, M-CSF, and G-CSF.

6. The method of claim 1, wherein the IGF-I is in a concentration of 100 μg/ml of medium.

7. The method of claim 1, wherein the G-CSF is in a concentration of 5 mg/ml, 50 mg/ml, or 500 mg/ml of medium.

8. The method of claim 1, wherein the M-CSF is in a concentration selected from the group consisting of 0.1 ng/ml, 0.3 ng/ml, 1.0 ng/ml, 3.0 ng/ml, 10 ng/ml, 30 ng/ml, and 100 ng/ml of medium.

9. The method of claim 2, wherein the IGF-I is in a concentration of 1 to 1000 μg/ml of medium.

10. The method of claim 2, wherein the M-CSF is in a concentration of from 1 to 1000 μg/ml of medium.

11. The method of claim 2, wherein the IGF-I is in a concentration of 100 ng/ml of medium.

12. The method of claim 2, wherein the M-CSF is in a concentration selected from the group consisting of 0.1 ng/ml, 0.3 ng/ml, 1.0 ng/ml, 3.0 ng/ml, 10 ng/ml, 30 ng/ml, and 100 ng/ml of medium.

13. The method of claim 3, wherein the IGF-I is in a concentration of from 1 to 1000 μg/ml of medium.

14. The method of claim 3, wherein the G-CSF is in a concentration of from 1 to 1000 μg/ml of medium.

15. The method of claim 3, wherein the IGF-I is in a concentration of 100 ng/ml of medium.

16. The method of claim 3, wherein the G-CSF is in a concentration of 5 mg/ml, 50 mg/ml, or 500 mg/ml of medium.

* * * * *